United States Patent [19]

Smith

[11] 4,117,603

[45] Oct. 3, 1978

[54] HIGH VACUUM FREEZE-DRYING

[76] Inventor: Walton J. Smith, Rte. 4, Grafton, N.H. 03240

[21] Appl. No.: 755,000

[22] Filed: Dec. 28, 1976

[51] Int. Cl.$^2$ .............................................. F26B 5/06
[52] U.S. Cl. ......................................................... 34/5
[58] Field of Search ....................................... 34/5, 92

[56] References Cited

U.S. PATENT DOCUMENTS

| | | | |
|---|---|---|---|
| 3,234,661 | 2/1966 | Nerge | 34/5 |
| 3,620,776 | 11/1971 | Mishkin | 34/5 |
| 3,653,929 | 4/1972 | Dwyer | 34/5 |
| 3,815,251 | 6/1974 | Gelder | 34/5 |
| 3,873,745 | 3/1975 | Rey et al. | 34/5 |

*Primary Examiner*—John J. Camby
*Attorney, Agent, or Firm*—Larson, Taylor and Hinds

[57] ABSTRACT

Water-soluble, substantially anhydrous materials such as anhydrous aspirin salt and anhydrous calcium aspirin salt, stable to hydrolysis, are prepared by subjecting a freeze-dried water-soluble material containing molecularly bound water which is susceptible to hydrolysis to a vacuum of 10 microns or less Hg to remove the molecularly bound water and condensing the removed water on a condenser below −50° C.

5 Claims, No Drawings

HIGH VACUUM FREEZE-DRYING

This invention relates to anhydrous materials and their preparation. It is particularly concerned with the removal of water bound by intermolecular forces from materials susceptible to hydrolysis, to provide an improved anhydrous product, for example the removal of the water of crystallization from low-stability or heat-unstable salts, for example, aspirin salts.

A well-known disadvantage of aspirin is its tendency to cause intestinal bleeding. To alleviate this difficulty, water-soluble salts of aspirin have been proposed, for example, sodium, potassium and calcium aspirins, or acetylsalicylates, aspirin being acetylsalicylic acid. The known salts are all somewhat hydrated and accordingly have poor stability and shelf life because the salt is slowly hydrolyzed and dissociates to form acetic acid and the corresponding salicylate.

These aspirin salts cannot be dried by heating as this provokes dissociation. It is known to freeze-dry sodium aspirin but the product still has an unsatisfactory shelf life. A shelf life of months or years is desirable.

It is an object of the present invention to provide an improved method of preparing anhydrous materials and to provide materials having a novel degree of hydration.

I have discovered that an improved anhydrous material can be prepared by freeze-drying a hydrated material susceptible to hydrolysis under conditions of ultra-high vacuum.

In conventional, commercial freeze-drying, the vacuum is generally about from 1 to 4 mm. Hg and is not sustained below 100 microns (0.1 mm. Hg). I provide a vacuum of at least 100 microns or preferably at least 50 microns, or preferably still, at least 10 microns or lower for a prolonged period at the final stage of freeze-drying. My invention is particularly applicable to commercial installations handling quantities of tens or hundreds of pounds or greater.

My invention is surprising because commercially it has not been feasible to reduce the pressure below 100 microns for a sustained period of time while drying. In practice, the low pressure environment includes a condenser. As ice builds up on the condenser, the surface temperature of the ice rises to at least $-40°$ C at which temperature the vapor pressure of water is 97 microns so that vacua substantially better than 100 microns cannot be obtained. Accordingly, I have found that it is desirable to maintain the condenser and the outer surface of the ice coating it at a temperature lower than $-50°$ C and preferably lower than $-75°$ C or lower even than $-100°$ C.

In previous freeze-drying manufacturing practice, rather low vacuums have been achieved at the beginning of the drying cycle which would have no benefit in this invention, since during the removal of the ordinary water not directly associated molecularly with the aspirin salt, any vacuum suitable for ordinary freeze-drying is suitable. The crucial period for obtaining the ultra-high-vacuum is at the end of the drying cycle when it is necessary to remove the water of hydration of the aspirin salt. This would normally come when the conditions in previous manufacturing practice is very unfavorable due to the heavy coat of ice on the condenser. Also, it should be taken note of that in ordinary practice, some heat is applied to the frozen mass to hasten drying also resulting in higher pressures. In commercial practice, the large equipment is never totally free of leaks, and this becomes a further negative factor in obtaining ultra-high vacuums.

In view of the importance of avoiding excessive build-up of ice on the condenser, it may be desirable to conduct the freeze-drying in two stages. Thus there can be a conventional first stage removing water from a frozen aqueous solution of the material under conventional conditions, i.e. at a temperature of from about $-20°$ C to about $-40°$ C and with a vacuum of from about 1 to 0.1 mm. Hg. There can then be a second stage under the conditions described above in which residual water, particularly water of hydration or crystallization is removed under a vacuum substantially better than 100 microns Hg. and a space temperature within the vessel of at least $-50°$ C to substantially reduce the residual water content of the material. The second stage can be conducted either in a new vessel commencing with an ice-free condenser, or after substantial removal of the ice accumulated in the first stage so that the desired temperature can be obtained. In most cases, the product of the first stage will be fairly stable and there will be no serious problem in transferring it between stages. This is the case, for example, with calcium aspirin.

Thus, using the freeze-drying techniques of my invention, products with substantially greater stability to hydrolysis and consequently good storage life can be obtained; it may be of course desirable to store them under anhydrous or low humidity conditions.

Several means are known for achieving the low temperatures required in practising my invention. For example, dry ice-acetone mixture can provide a temperature of about $-86°$, and dry ice-ether about $-100°$ C. whilst liquid gases, e.g. liquid air, will provide much lower temperatures. Mechanical refrigeration also is a suitable means.

Of particular interest in practicing my invention is calcium aspirin which has a high degree of solubility and apparently has a reduced tendency to irritate the stomach lining and cause intestinal bleeding.

The literature indicates that calcium aspirin crystallizes with seven molecules of water, where only one molecule of water would be adequate to decompose the entire molecule. I have discovered I can prepare calcium aspirin in aqueous solution without substantial decomposition, and then freeze the solution and freeze-dry the mixture to obtain a product when flavored results in a product which can be readily reconstituted for safe use by people having difficulty swallowing pills and for other benefits disclosed in a patent application now pending in my behalf.

When producing calcium aspirin using the previous disclosures, a product results which contains ½ to 1 molecule of water, and I have found that this product does not have an adequate shelf life at room temperature to justify marketing it. Patents by other workers have disclosed freeze-drying of sodium aspirin by a similar process, but no product has ever been marketed to date because of their poor shelf lifes. Using other methods of producing a calcium aspirin such as in anhydrous alcohol products have been made and marketed, but so many problems of stability were encountered that, to date, nowhere in the world is calcium aspirin, or any other mono- or divalent salt of aspirin marketed as such despite its many potential benefits, so far as I know.

In addition to Aspirin salts, there are many other types of compounds which are of pharmaceutical and other importance whose stabilities can be increased by making them anhydrous as opposed to the hydrate form. The antibiotic, Tetracycline, is an example of this class of compound which forms a hydrate which must ordinarily be heated to 60° in vacuum and dried for 8 hours to make it anhydrous. Using the process mentioned above, this compound can be dried economically at room temperature or lower to form the anhydrous product without decomposition.

EXAMPLE 1

Anhydrous Calcium Aspirin

The product made by reaction of Aspirin with Calcium Carbonate in water, filtering, freezing, and freeze-drying using the technique described in a parallen application, is used for the present example.

Twenty grams of Calcium Aspirin Hydrate, freeze-dried, is placed in a desiccator connected via a 29/42 joint to a condenser with an equal free space which in turn is cooled with a mixture of acetone-dry ice (excess of latter) and subjected to a vacuum pump capable of obtaining a vacuum in a closed system in the absence of water vapor of 0.1 microns. Without any additional heating, the vacuum was maintained for a period of 48 hours during which time there was a weight loss demonstrating a loss of water making the product substantially anhydrous. The product was demonstrated to be substantially free of free salicylic acid, and to have greatly enhanced stability at room temperature as compared to the starting material, namely the freeze-dried Calcium Aspirin Hydrate.

EXAMPLE 2

Calcium Aspirin with Starch Hydrolyzate

This is an example of freeze-drying of the hydrate obtained by the combination of Calcium Aspirin and Hydrolyzed low DE starch (Maltrin as produced by Grain Processing Co., Muscatine, Iowa). Such a hydrate with Maltrin 10 was subjected to the same treatment as the Calcium Aspirin in Example 1 with the result that the anhydrous form resulted, and it was shown to have a very low moisture content and had a similar stability as the product obtained in Example 1. While the use of starch hydrolysate produces a harder, more granular product, having some commercial advantages, it is necessary to remove the stronly held water from the starch hydrolysate to the same extent as the aspirin salt.

EXAMPLE 3

Tetracycline Base

The hydrate was subjected to the same treatment as the Calcium Aspirin in Example 1 with the result that the anhydrous form was obtained without any substantial outside or external warming other than that which came from the surrounding room.

It is obvious that with higher vacua and with condenser temperatures cooled with liquid nitrogen or other means of obtaining lower temperatures than the above would offer certain advantages.

My invention also includes novel products of this process, notable for their unusually lower water contents, e.g. substantially anhydrous calcium or sodium aspirin having less than 1/10th mole equivalents of water per mole equivalent of the salt or freeze-dried anhydrous tetracycline base.

In general, the indicated 1/10th mole equivalent water presents a substantial advantage, but I prefer 1/100th or less.

I claim:

1. A method of preparing a water-soluble, substantially anhydrous material stable to hydrolysis comprising subjecting a freeze-dried, water-soluble material containing molecularly bound water which is susceptible to hydrolysis to a vacuum of 10 microns or less Hg to remove said molecularly bound water and condensing the removed water on a condenser below −50° C.

2. A water-soluble, substantially anhydrous aspirin salt stable to hydrolysis.

3. A water-soluble, substantially anhydrous calcium aspirin salt stable to hydrolysis.

4. A method of preparing water-soluble, substantially anhydrous apsirin salt stable to hydrolysis comprising subjecting a frozen aqueous solution of an aspirin salt to freeze drying at a temperature of about −20° to about −40° C under a vacuum of about 1 to about 0.1 microns Hg to provide a freeze-dried aspirin salt containing molecularly bound water which is susceptible to hydrolysis, subjecting said freeze-dried salt to a second freeze drying at a vacuum of 10 microns or less Hg to remove molecularly bound water and condensing said water on a condenser below −50° C.

5. The method of claim 4 wherein the aspirin salt is a calcium aspirin salt.

* * * * *